(12) United States Patent
Fujita

(10) Patent No.: US 8,303,486 B2
(45) Date of Patent: Nov. 6, 2012

(54) CAPSULE-TYPE ENDOSCOPE SYSTEM, AND PROGRAM AND METHOD USED FOR THE SYSTEM

(75) Inventor: Manabu Fujita, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1188 days.

(21) Appl. No.: 12/134,775

(22) Filed: Jun. 6, 2008

(65) Prior Publication Data

US 2008/0306341 A1 Dec. 11, 2008

(30) Foreign Application Priority Data

Jun. 6, 2007 (JP) ................................ 2007-150675

(51) Int. Cl.
*A61B 1/00* (2006.01)
(52) U.S. Cl. ...................................................... 600/118
(58) Field of Classification Search .................. 600/109, 600/118
See application file for complete search history.

(56) References Cited

U.S. PATENT DOCUMENTS

| | | | |
|---|---|---|---|
| 5,609,285 A | 3/1997 | Grant et al. | |
| 5,632,433 A | 5/1997 | Grant et al. | |
| 6,443,909 B1 | 9/2002 | Ouchi | |
| 7,843,329 B2 * | 11/2010 | Shigemori | 340/539.12 |
| 2004/0243108 A1 | 12/2004 | Suzuki | |
| 2005/0171418 A1 * | 8/2005 | Lin | 600/407 |
| 2006/0095093 A1 | 5/2006 | Bettesh et al. | |
| 2006/0229644 A1 | 10/2006 | Kortenbach | |
| 2007/0081077 A1 | 4/2007 | Matsui | |
| 2008/0262298 A1 * | 10/2008 | Mori | 600/109 |
| 2009/0043157 A1 * | 2/2009 | Hirakawa et al. | 600/109 |
| 2009/0259096 A1 * | 10/2009 | Shigemori et al. | 600/109 |
| 2009/0312601 A1 * | 12/2009 | Shigemori | 600/103 |
| 2010/0094104 A1 * | 4/2010 | Nagase et al. | 600/302 |

FOREIGN PATENT DOCUMENTS

| | | |
|---|---|---|
| DE | 8808285 U1 | 8/1988 |
| EP | 1454588 A2 | 9/2004 |
| JP | 2001-275950 | 10/2001 |
| JP | 2005-296186 | 10/2005 |
| JP | 2006-020971 | 1/2006 |
| JP | 2006-061470 | 3/2006 |

(Continued)

OTHER PUBLICATIONS

European Office Action dated Jun. 7, 2010.

(Continued)

*Primary Examiner* — W. B. Perkey
(74) *Attorney, Agent, or Firm* — Scully, Scott, Murphy & Presser, P.C.

(57) ABSTRACT

A capsule-type endoscope system includes plural receivers, plural mounting spots for mounting the receivers and an information processing apparatus connected to the receivers via the mounting spots. Each receiver wirelessly receives image data from a capsule-type endoscope that images inside of an examinee's body; stores examinee identification information and the received image data; and displays the examinee identification information or examinee information associated therewith. The information processing apparatus receives the examinee identification information from each receiver via the mounting spot and manages its correlation with receiver identification information or mounting spot identification information. The image data is transmitted via the mounting spot to the information processing apparatus to be stored therein. The information processing apparatus displays the correlation by displaying at least a part of the examinee identification information or examinee information, and displays the progress of the transmission of image data corresponding to each receiver.

20 Claims, 12 Drawing Sheets

FOREIGN PATENT DOCUMENTS

| | | |
|---|---|---|
| JP | 2006-130322 | 5/2006 |
| JP | 2006-239309 | 9/2006 |
| JP | 2006-288542 | 10/2006 |
| WO | WO 2005/062715 A2 | 7/2005 |
| WO | WO 2006/003650 A2 | 1/2006 |
| WO | WO 2007/074712 A1 | 7/2007 |

OTHER PUBLICATIONS

Extended Supplementary European Search Report dated Jun. 4, 2010.

International Search Report dated Aug. 5, 2008 from related application PCT/JP2008/001420.

* cited by examiner

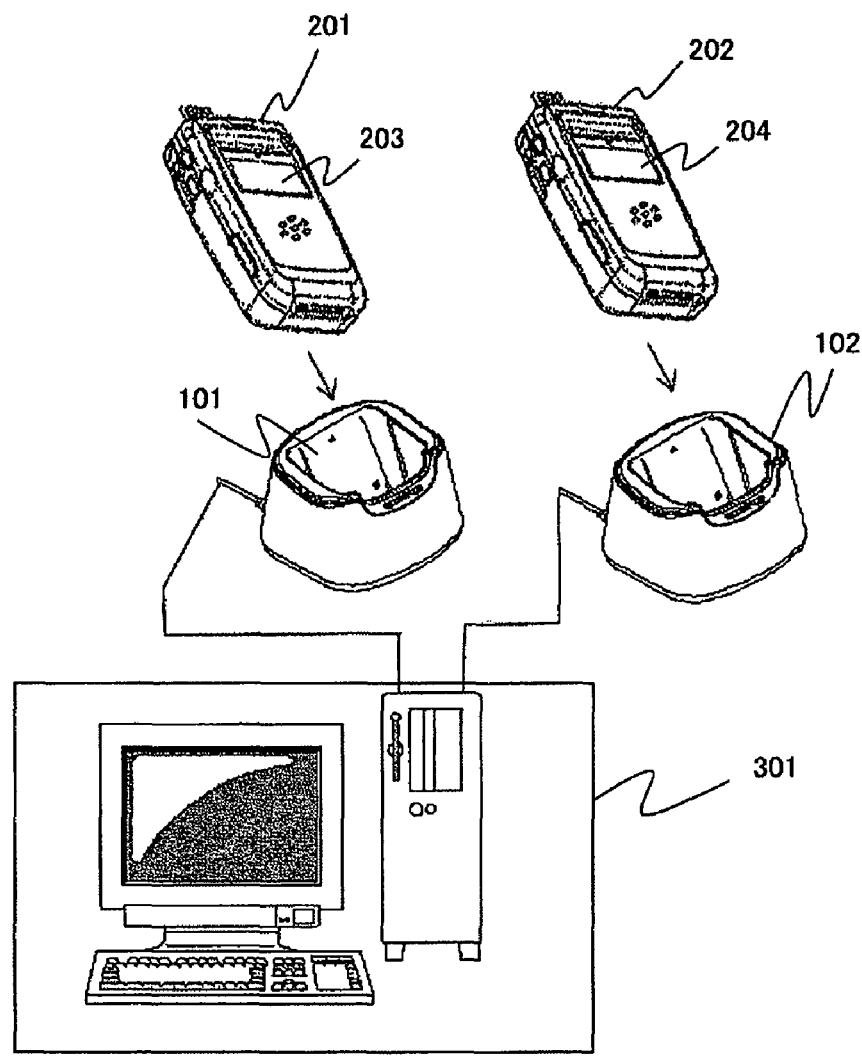
F I G. 1

SLOT CORRESPONDENCE TABLE 401

| SLOT ID | PATIENT INFORMATION |
|---|---|
| PORT ADDRESS 411 | PATIENT INFORMATION 422 |
| PORT ADDRESS 412 | PATIENT INFORMATION 421 |

F I G. 3

501

```
CRADLE 101
    PATIENT ID    O 1
    SEX           MALE
    BIRTH DATE    1950/05/05
CRADLE 102
    PATIENT ID    O 2
    SEX           FEMALE           [INITIALIZE]
    BIRTH DATE    1953/04/04
```

```
PATIENT ID   O 1
SEX          MALE
BIRTH DATE   1950/05/05
```
502

```
PATIENT ID   O 2
SEX          FEMALE
BIRTH DATE   1953/04/04
```
503

F I G. 5

```
504
┌─────────────────────────────────────────┐
│ CRADLE 101                              │
│     PATIENT ID      O 2                 │
│     SEX             FEMALE              │
│     BIRTH DATE      1953/04/04   ┌────────┐
│ CRADLE 102                       │ START  │
│     PATIENT ID      O 1          │TRANSFER│
│     SEX             MALE         └────────┘
│     BIRTH DATE      1950/05/05          │
└─────────────────────────────────────────┘
```

F I G. 6

505

```
CRADLE 101
    PATIENT ID      O 2      [▰▱▱▱]
    SEX             FEMALE
    BIRTH DATE      1953/04/04
CRADLE 102
    PATIENT ID      O 1      [▱▱▱▱]
    SEX             MALE
    BIRTH DATE      1950/05/05
```

F I G.  7

SLOT CORRESPONDENCE TABLE 402

| RECEIVER ID | PATIENT INFORMATION |
|---|---|
| 3457 | O 1, MALE, 1950/05/05 |
| 3458 | O 2, FEMALE, 1953/04/04 |

FIG. 12

CAPSULE-TYPE ENDOSCOPE SYSTEM, AND PROGRAM AND METHOD USED FOR THE SYSTEM

CROSS REFERENCE TO THE RELATED APPLICATION

This application is based upon and claims the benefit of priority from the prior Japanese Patent Application No. 2007-150675, filed Jun. 6, 2007, the entire contents of which are incorporated herein by reference.

BACKGROUND OF THE INVENTION

1. Field of the Invention

The present invention relates to a technique for managing a data transmission performed for utilizing, in an information processing apparatus, image data transmitted from a capsule-type endoscope to a receiver.

2. Description of the Related Art

Endoscopes are often used for observing inside of a human body in recent years. An endoscope includes an imaging unit so that the image data obtained by imaging inside of a human body by the imaging unit is transmitted to an external apparatus and an image is displayed. A physician observes the displayed image and performs a diagnosis, an operation and other medical procedures. The image data is transmitted from the endoscope to an external apparatus by way of a cable or using radio communications. The latter type of endoscope is also called a wireless endoscope. To use it, a receiver is required to receive the image data transmitted by way of the radio communication.

As an example, reference patent document 1 notes a surgery apparatus including one unit of wireless endoscope and two units of transmitting and receiving apparatuses. The two transmitting and receiving apparatuses severally receive image data from the wireless endoscope. Even if a reception failure occurs in one transmitting and receiving apparatus, the image data is transferred thereto after received at the other transmitting and receiving apparatus from the wireless endoscope, and therefore the reception condition can be recovered to a good condition.

Meanwhile, the wireless endoscopes also include a type called a capsule-type endoscope, which is used in combination with a portable receiver equipped on an examinee. A capsule-type endoscope includes an imaging unit and a wireless transmission unit for transmitting image data obtained by imaging to an external apparatus by way of a wireless communication. The capsule-type endoscope is used as follows.

First, the examinee swallows the capsule-type endoscope which proceeds in the examinee's body by means of the peristaltic movement of the digestive canal in about eight hours and which is eventually ejected from the body. While the capsule-type endoscope is within the body, the image data obtained by the imaging unit performing imaging operation is transmitted by the wireless transmission unit so as to be received by the receiver. The receiver stores the received image data in a built-in storage unit or a removably attached storage medium. If the imaging unit is configured to image, for example, two times per second, the image data equivalent to approximately 60,000 images is accumulated in about eight hours.

The image data accumulated in the receiver is transmitted to an information processing apparatus such as a work station after the capsule-type endoscope is ejected out of the examinee's body. The transmission takes relatively a long period of time. As an example, if approximately 60,000 images are accumulated in the receiver throughout one examination as described above, it sometimes take tens of minutes to transmit the vast amount of the image data. Those pieces of image data transmitted to the information processing apparatus are displayed on a display apparatus as images so as to be observed by a physician and other medical staff.

As the popularization of the capsule-type endoscope progresses, there will predictably be an increase in a plurality of examinees using the capsule-type endoscopes simultaneously or successively in a single hospital or inspection agency. This prompts a need to solve a problem or problems particular to a plurality of receivers existing.

For example, one of such problems is a possibility of misidentification of an examinee when equipping the examinee with a receiver. Reference patent document 2 notes a receiver (i.e., an external device) importing the identification information specific to an examinee (i.e., a subject) and storing and displaying it in order to prevent such misidentification. The identification information, for example, concerns the name, birth date, sex, et cetera, of an examinee. A physician or another medical staff collates the identification information displayed on the receiver with the examinee, thereby enabling a prevention of misidentifying the examinee as other examinees. The identification information is read from the work station and imported into the receiver. For importing the identification information, a detachably attached portable storage medium may be used or the receiver may be connected to the work station via a cradle.

The problem specific to a plurality of receivers existing is not limited to a misidentification of examinees. With respect to managing transmissions of respective pieces of image data from a plurality of receivers, what are required to be devised include improvements in efficiency, operability and/or convenience.

As an example, when the N-number of examinees are simultaneously examined by using capsule-type endoscopes, the operator of a capsule-type endoscope system carries out a process for transmitting respective pieces of image data from the N units of receivers to an information processing apparatus such as a work station after finishing the examination of N examinees. This process may be carried out by, for example, connecting one receiver to the information processing apparatus and performing a transmission from the receiver, followed by repeating a step of changing over the receiver to the next receiver, which are connected to the information processing apparatus, upon completing the present transmission and a step of performing the transmission from the replaced new receiver.

Such a method, however, requires an operator involvement and manual work every time the receivers are replaced. Further, if an operation and management method in need of a constant operator standby for the involvement and manual work is adopted, the operator is unnecessarily retained because the transmission of image data requires relatively a long period of time as described above, and therefore the work efficiency is not good. Further, it might be possible for an operator to replace the receivers every time the transmission from one receiver is completed, while the operator is engaged in another work. In this case, however, the operator is required to interrupt the other work for any number of times.

Accordingly, a contrivance is made to improve the work efficiency in the case, in which a receiver is configured to accumulate image data in a removable storage medium, by processing M-piece of storage media taken out of M-unit of receivers in a lump and thereby the frequency of the operator intervention is reduced.

For example, it is feasible to adopt a method to connect a storage media reader having four slots to an information processing apparatus for use in the transmission of image data, in which case the M=4. In this method, an operator takes out the storage media respectively from the four receivers, inserts the four storage media into the four slots, respectively, and instructs the information processing apparatus to start transmission, the mere operation of which causes the image data for the respective four examinees to be automatically and sequentially transmitted to the information processing apparatus. Therefore, the operator is relieved from waiting in front of the information processing apparatus for a period of time until the transmission of the image data for the four examinees is completed, enabling her/him to be engaged in another work without being interrupted.

If the receiver is configured to accumulate image data in a built-in storage unit, in place of a removable storage medium, however, the aforementioned method can not be adopted, and therefore the work efficiency and convenience of the operator is not sufficiently supported.

Further, if a plurality of examinees has to be examined one after another, there is sometimes a need to reuse the storage medium and/or receiver as soon as the transmission of image data is completed. For example, in the example method using the storage media reader having four slots as described above, there is sometimes a need to take a first storage medium from the reader and reuse the first storage medium when the transmission of the image data from the first storage medium is completed. The appearance of the storage medium, however, does not indicate as to which storage medium corresponds to which examinee, and therefore the operator has not conventionally been able to easily determine as to which storage medium to be taken out from the reader for a reuse. That is, the storage media have not been enabled for an efficient reuse through a simple operation, which has been sometimes inconvenient.

Patent document 1: Laid-Open Japanese Patent Application Publication No. 2001-275950
Patent document 2: Laid-Open Japanese Patent Application Publication No. 2005-296186

As described above, there is a factor undermining the work efficiency of an operator and the reuse efficiency of a receiver related to the transmission of image data from the receiver to information processing apparatus in the case of a plurality of receivers existing to receive the image data from capsule-type endoscopes. That is, there is a room in the conventional system for improving the efficiency, operability or convenience.

SUMMARY OF THE INVENTION

In consideration of the above description, the present invention aims at improving the efficiency, operability or convenience related to the transmission of image data, to an information processing apparatus, from a plurality of receivers which has received image data from capsule-type endoscopes.

According to the present invention, a capsule-type endoscope system includes a plurality of receivers each for receiving, from a capsule-type endoscope by way of a wireless communication, image data of an observation image of inside of a body of an examinee imaged by the capsule-type endoscope; a plurality of mounting spots for respectively mounting the plurality of receivers; and an information processing apparatus connected to the plurality of receivers by way of the respective mounting spots.

Each of the plurality of receivers includes a first storage unit and a first display unit. The first storage unit stores the received image data and examinee identification information identifying the examinee. The first display unit displays the examinee identification information or examinee information about the examinee that is associated with the examinee identification information.

Further, the information processing apparatus includes a management unit for receiving the examinee identification information from each of the plurality of receivers by way of each of the plurality of mounting spots and managing correlation between the received examinee identification information and receiver identification information identifying the receiver or mounting spot identification information identifying the mounting spot on which the receiver is mounted; a second storage unit; and a second display unit.

The image data is transmitted to the information processing apparatus by way of each of the plurality of mounting spots and stored in the second storage unit. The second display unit displays the correlation by displaying at least a part of the examinee identification information displayed on the first display unit or a part of the examinee information displayed on the first display unit. The second display unit further displays a progress of the transmission of the image data corresponding to each of the plurality of receivers.

A program according to the present invention is a program for causing the information processing apparatus in the capsule-type endoscope system to perform the above described management and display of the correlation and the above described display of the progress. The program is stored in a computer readable storage medium. A method according to the present invention is a method executed by the information processing apparatus in accordance with the program.

The present invention enables the connection of a plurality of receivers, each of which comprises the first storage unit, to an information processing apparatus by way of a plurality of mounting spots in a lump. The present invention is also contrived such that the progress of the transmission is displayed on the second display unit, and such that the correlation of the mounting spot identification information or receiver identification information with the examinee identification information implies the examinee identification information or examinee information.

BRIEF DESCRIPTION OF THE DRAWINGS

FIG. 1 is the external appearance diagrams of devices constituting a capsule-type endoscope system according to a first embodiment of the present invention;

FIG. 3 is a diagram exemplifying a slot correspondence table according to a first embodiment of the present invention;

FIG. 5 is a diagram exemplifying a screen displayed at initialization, according to a first embodiment of the present invention;

FIG. 6 is a diagram exemplifying the screen of an observation apparatus when two receivers are mounted onto respective cradles after the completion of examinations, according to a first embodiment of the present invention;

FIG. 7 is a diagram exemplifying the screen of an observation apparatus when image data is transferred from a receiver in a first embodiment of the present invention;

FIG. 12 is a diagram exemplifying a slot correspondence table according to a third embodiment of the present invention.

DESCRIPTION OF THE EMBODIMENTS

Figure 2:
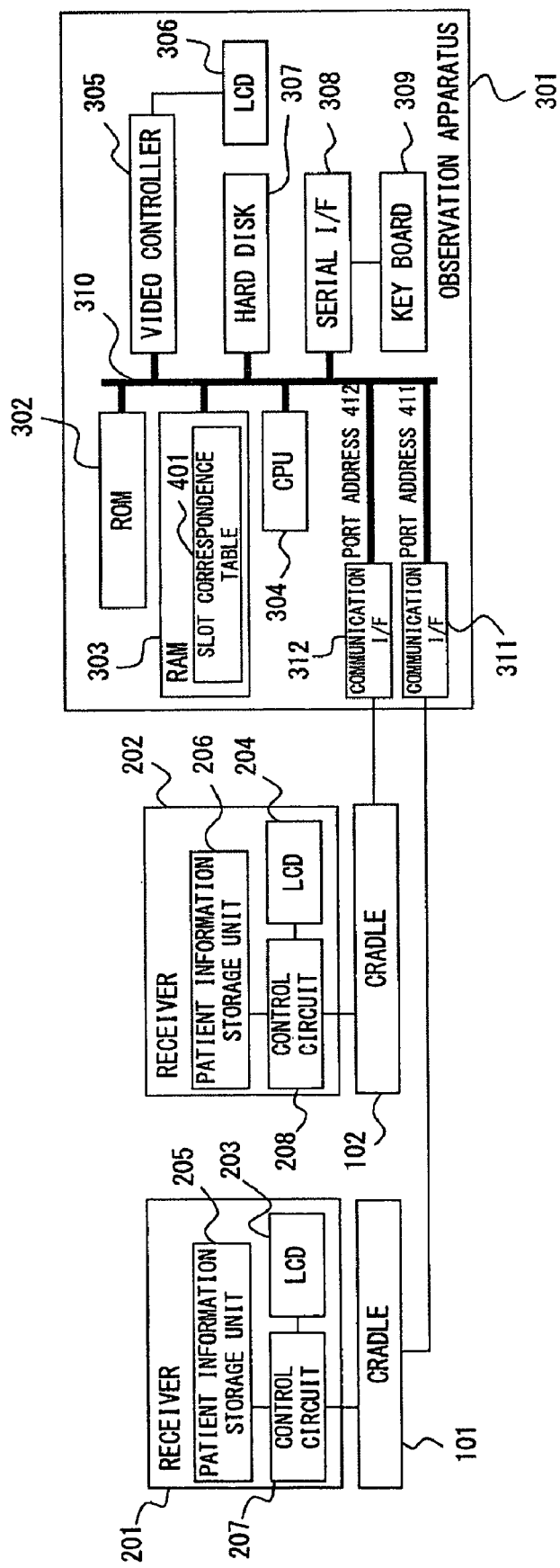
FIG. 2 is a block diagram showing the configuration of a capsule-type endoscope system according to a first embodiment of the present invention.

The following is a description, in detail, of the embodiments of the present invention by referring to the accompanying drawings.

FIG. 1 is the external appearance diagrams of devices constituting a capsule-type endoscope system according to a first embodiment of the present invention. The capsule-type endoscope system shown in FIG. 1 includes two receivers 201 and 202, and an observation apparatus 301, with the receivers 201 and 202 enabled to be connected to the observation apparatus 301 by way of respective cradles 101 and 102. FIG. 1 shows, for simplicity, respective two units of the receivers and cradles; the numbers of units are discretionary, that is, three or more, respectively. Besides, the numbers of receivers and cradles may not necessarily be the same.

The receiver 201 is a portable device attached to a patient (not shown in a drawing herein). Note that the following embodiments use the word "patient" in the same meaning as a general examinee. While a capsule-type endoscope (not shown in a drawing herein; also simply noted as "capsule endoscope" hereinafter) stays inside of a patient's body, the receiver 201 receives image data obtained by imaging inside of the patient's body from the capsule endoscope by way of a wireless communication and stores the image data. An external surface of the receiver 201 is equipped with a display unit 203 of which the display examples are described later. The receiver 202 is also configured the same as the receiver 201 and is equipped with a display unit 204 in an external surface.

The observation apparatus 301 is an information processing apparatus such as a general purpose workstation. The cradle 101 is connected to the observation apparatus 301 by way of a cable. Mounting the receiver 201 on the cradle 101 enables a data transmission between the receiver 201 and observation apparatus 301 via the cradle 101. The cradle 102 is likewise connected to the observation apparatus 301 by way of a cable. Then, mounting the receiver 202 on the cradle 102 enables a data transmission between the receiver 202 and observation apparatus 301 via the cradle 102.

FIG. 1 shows the case of the receiver 201 mounted on the cradle 101 and the receiver 202 mounted on the cradle 102; the relationship between a receiver and a cradle is not fixed as described later, and instead the mounting of any receiver on any cradle is discretionary.

FIG. 2 is a block diagram showing the configuration of a capsule-type endoscope system according to the first embodiment of the present invention. Similarly to FIG. 1, FIG. 2 also shows the case of the receivers 201 and 202 being respectively mounted on the cradles 101 and 102.

As shown in FIG. 2, the present first embodiment is configured to use a liquid crystal display (LCD) 203 for the display unit 203 of the receiver 201. The LCD 203 corresponds to the above-noted first display unit. The display unit 203 is not limited to an LCD and instead may use an element, such as an electroluminescence (EL) element, which is also suitable to a portable device. The receiver 201 also includes a wireless reception unit (not shown in a drawing herein) for receiving image data transmitted from a capsule endoscope byway of a wireless communication.

The receiver 201 further includes a patient information storage unit 205 for storing information such as the image data received from the capsule endoscope and patient ID described later, and includes a control circuit 207 for controlling various processes.

The patient information storage unit 205 corresponds to the above-noted first storage unit and is a built-in storage unit implemented by, for example, a hard disk, flash memory and the like. The control circuit 207 controls various processes, for example, the following paragraphs (a) through (c).

(a) The process for writing, to the patient information storage unit 205, data transmitted from the observation apparatus 301 by way of the cradle 101;

(b) The process for reading data from the patient information storage unit 205 and transmitting it to the observation apparatus 301 by way of the cradle 101; and (c) The process for reading necessary data from the patient information storage unit 205 and displaying it in the LCD 203.

Likewise the receiver 201, the receiver 202 also includes an LCD 204, a wireless communication unit (not shown in a drawing herein), a patient information storage unit 206 and a control circuit 208.

The observation apparatus 301 includes read only memory (ROM) 302, random access memory (RAM) 303, a central processing unit (CPU) 304, a video controller 305, a hard disk 307, a serial interface (I/F) 308, a communication I/F 311 and a communication I/F 312, with a bus 310 interconnecting these constituent components. Further, an LCD 306 is connected to the video controller 305, and a key board 309 is connected to the serial I/F 308. Also, a mouse (not shown in a drawing herein) or the like may be connected to the serial I/F 308.

The ROM 302 or hard disk 307 stores a program that is loaded onto the RAM 303 and executed by the CPU 304. With this configuration, various controls described later are implemented. Further, the program may be stored in a computer readable portable storage medium. Connecting the drive apparatus (not shown in a drawing herein) of the portable storage medium to the observation apparatus 301 enables it to read the program from the portable storage medium and copy the program to the hard disk 307.

The video controller 305 controls the display onto the LCD 306 in accordance with the instruction from the CPU 304. The example display of the LCD 306 is described later. The LCD 306 corresponds to the above-noted second display unit.

The hard disk 307 stores image data transmitted from the receiver 201 or 202 by way of the cradle 101 or 102. The hard disk 307 corresponds to the above-noted second storage unit.

An instruction input by an operator using the key board 309 is reported to the CPU 304 by way of the serial I/F 308.

Port addresses 411 and 412 are assigned respectively to the communication I/Fs 311 and 312. Further, the communication I/Fs 311 and 312 are respectively connected to the cradles 101 and 102 by way of respective cables.

When the receiver 201 or 202, either one of which is dismounted from the patient, and retrieved, after the completion of examination, is mounted onto the cradle 101 or 102, the communication I/F 311 or 312 detects the event. With the detection of the event used as trigger, a record is added to a slot correspondence table 401 retained in the RAM 303. Comparably, when the receiver 201 or 202 is detached from the cradle 101 or 102, the communication I/F 311 or 312 also detects the event and, with the detection of the event used as trigger, a record is eliminated from the slot correspondence table 401. The details of the slot correspondence table 401 are described later. The present embodiment is configured such that the communication I/Fs 311 and 312, CPU 304 and RAM 303 realize the above-noted management unit.

Further, the above-noted mounting spot corresponds to the respective slots of the cradles 101 and 102 according to the present embodiment. The slot is a concave part equipped on the cradle for mounting a receiver as shown in FIG. 1 so that the receiver and cradle are electrically interconnected by mounting the receiver onto (i.e., inserting it into) the slot. Two units of receivers can be connected together to the observation apparatus 301 by means of the cradles 101 and 102 respectively having slots each corresponding to a mounting spot and cables connecting the cradles 101 and 102 to the observation apparatus 301.

Next is a description of the slot correspondence table by referring to FIG. 3. FIG. 3 is a diagram exemplifying a slot correspondence table according to the first embodiment of the present invention. The slot correspondence table 401 shown in FIG. 3 is a table for managing the correlation between information identifying a slot and information identifying a patient to whom the receiver inserted into the slot was attached.

The example of FIG. 3 calls the information identifying a slot as "slot ID". Identifying a slot makes it possible to identify a receiver inserted into the slot indirectly. Further, the slot correspondence table 401 shown in FIG. 3 may include information associated with a patient ID, such as the sex and/or birth date of a patient, in addition to the patient ID that is the information identifying the patient. The patient ID and information such as the sex and/or birth date are hereinafter collectively called "patient information".

The slot correspondence table 401 utilizes the port address of the observation apparatus 301 as a slot ID. The reason for this is as follows.

As shown in FIG. 1, the present embodiment is configured to have only one slot in a single cradle. Further, one cradle corresponds to one communication I/F and each unique port address is assigned to each communication I/F as is clear from FIG. 2. Further, the present embodiment premises that, once cradles are connected to the observation apparatus 301, a capsule-type endoscope system is basically operated continually without changing the manner of connecting the cables between the respective cradles and observation apparatus 301. Therefore, it is possible to uniquely identify a slot on the basis of the port address. This is why the example of FIG. 3 utilizes a port address as a slot ID.

In specific, the first record in the slot correspondence table 401 expresses that the port address 411 corresponds to the patient information 422, and the second record expresses that the port address 412 corresponds to the patient information 421. As shown in FIG. 2, the port addresses 411 and 412 are respectively assigned to the communication I/Fs 311 and 312. Further, the communication I/Fs 311 and 312 are respectively connected to the cradles 101 and 102. The premise is that the connection is fixed as described above and that the correlation between the communication I/F and cradle will not be changed.

Therefore, the slot correspondence table 401 shown in FIG. 3 expresses the following paragraphs (a) and (b).

(a) A receiver accumulating the image data of a patient represented by the patient information 422 is mounted onto the cradle 101; and (b) A receiver accumulating the image data of a patient represented by the patient information 421 is mounted onto the cradle 102.

Further, the slot correspondence table 401 is stored in the RAM 303, and a record of the slot correspondence table 401 is created or deleted, which is triggered by the event, that is, the establishment or elimination of the connection between the cradle and receiver, as described by referring to FIG. 2.

Next is a description of the process flow and screen examples in a utilization example of a capsule-type endoscope system according to the first embodiment of the present invention by referring to FIGS. 4 through 7.

Figure 4:
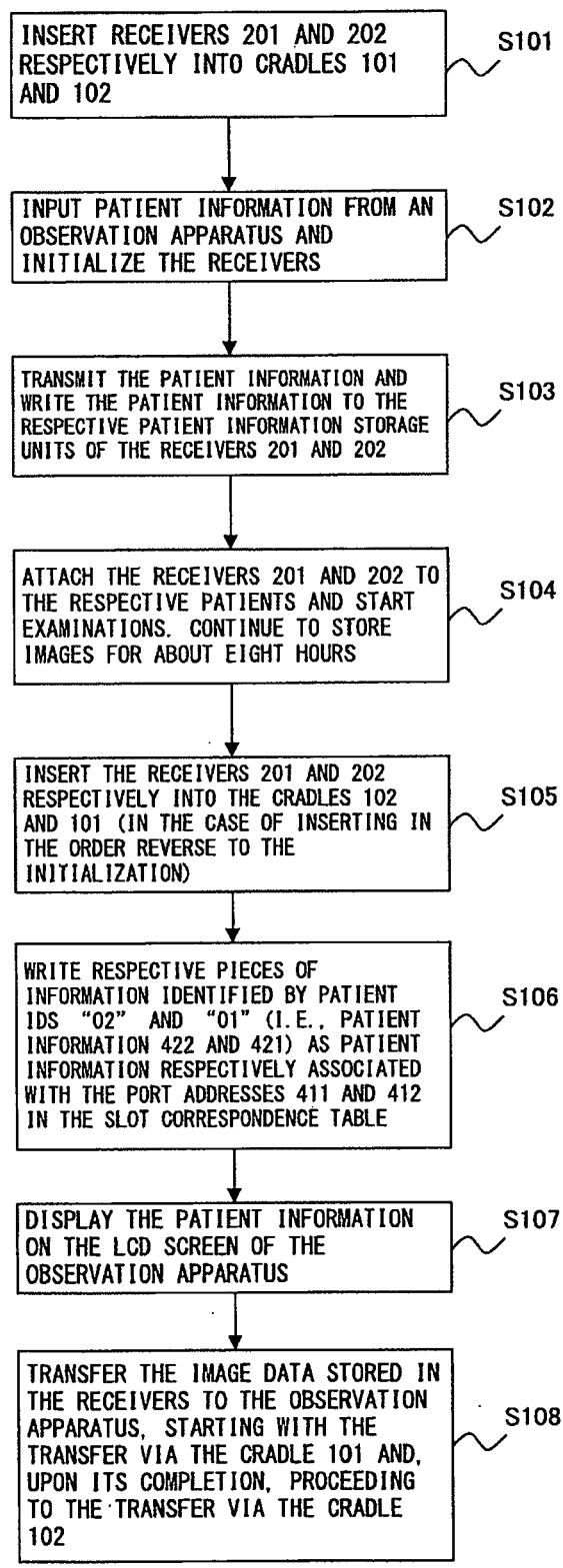
FIG. 4 is a flow chart exemplifying the utilization of a capsule-type endoscope system according to a first embodiment of the present invention.

FIG. 4 is a flow chart exemplifying the utilization of a capsule-type endoscope system according to the first embodiment of the present invention. FIG. 4 exemplifies the case of simultaneously examining two patients identified by "01" and "02" as the patient IDs.

In step S101 (also simply noted as "S101" hereinafter), the operator inserts the receivers 201 and 202 respectively into the slots of the cradles 101 and 102. That is, the operator mounts the receivers 201 and 202 onto the respective cradles 101 and 102. This enables a data transmission between the receiver 201 and observation apparatus 301, and also a data transmission between the receiver 202 and observation apparatus 301.

Then in S102, the operator, operating the key board 309 of the observation apparatus 301, inputs the patient information of the two patients, who are examination targets, and also gives an instruction to initialize the receivers 201 and 202 mounted onto the cradles 101 and 102.

For describing the details of the process of S102, first, the following two are given as the premises.

The first premise is that the operator or another medical staff has predetermined the following paragraphs (a) and (b).

(a) The receiver 201 mounted on the cradle 101 shall be attached on a patient identified by "01" as the patient ID; and (b) The receiver 202 mounted on the cradle 102 shall be attached on a patient identified by "02" as the patient ID.

The second premise is that a database storing various pieces of information related to patients exists in the hard disk 307 of the observation apparatus 301 shown in FIG. 2 or in a storage apparatus (not shown in a drawing herein) connected to the observation apparatus 301 by way of a network. Therefore, the operator is enabled to call up information such as name, sex, birth date, medical history, et cetera, related to a patient ID just by inputting, for example, the patient ID from the key board 309 in S102.

Under these premises, the process of S102 is further specifically described by referring to FIG. 5 that shows a screen example indicated in S102.

In accordance with the first premise, the operator inputs a value "01" as a patient ID corresponding to the cradle 101, and inputs a value "02" as a patient ID corresponding to the cradle 102. This prompts to call up pieces of the patient information indicating the sex and birth date from the database, from among pieces of the patient information of the two patients, on the basis of the second premise. The called-up patient information is displayed on the screen 501 of the LCD 306 of the observation apparatus 301, with respective pieces of the called-up patient information respectively correlated with cradle IDs, written as "cradle 101" and "cradle 102", which identify the respective cradles, as shown in FIG. 5.

Further, the screen 501 also displays a button labeled "initialize" for instructing the receivers 201 and 202 to initialize themselves. The operator uses, for example, a mouse to click on the "initialize" button, thereby making it possible to instruct, from the observation apparatus 301 by way of the cradles 101 and 102, the receivers 201 and 202 to initialize them per se.

Returning to the description of FIG. 4 at this moment and proceeding to S103 following S102, the observation apparatus 301, in accordance with the operator's input in S102, transmits the respective pieces of patient information of the two patients to the receivers 201 and 202 and instructs the receivers 201 and 202 to initialize themselves. The patient information transmitted in S103 according to the present embodiment is the patient ID, sex and birth date.

Then, the control circuit 207 of the receiver 201 performs a control for initializing the patient information storage unit 205 in accordance with the instruction. The initialization of the patient information storage unit 205 includes the processes of the following paragraphs (a) through (c).

(a) The process for writing, to the patient information storage unit 205, the patient information transmitted from the observation apparatus 301;
(b) The process for displaying the written patient information on the LCD 203; and
(c) The process for erasing the image data accumulated when the receiver 201 is used in the previous job if the image data remains.

Likewise, the control circuit 208 of the receiver 202 also initializes the patient information storage unit 206.

As a result, the screen 502 of the LCD 203 of the receiver 201 displays the same patient ID, sex and birth date as those transmitted from the observation apparatus 301 as shown in FIG. 5. Likewise, the screen 503 of the LCD 204 of the receiver 202 also displays the same patient ID, sex and birth date as those transmitted from the observation apparatus 301. This configuration enables the operator to confirm whether or not the receivers 201 and 202 have been correctly initialized, by visually comparing the screens 501, 502 and 503. Note that the slot correspondence table 401 shown in FIG. 3 has not been used during the processes up to S103 and therefore no record exists in the table.

Having confirmed that the receivers 201 and 202 have been correctly initialized in S103, the operator, a nurse or other medical staff attaches the receiver 201 to a patient whose patient ID is "01" and attaches the receiver 202 to a patient whose patient ID is "02", in S104. Then, these patients respectively swallow capsule endoscopes, and the respective examinations start. As described above, the capsule endoscope moves through inside of the patient in about eight hours, during which time the inside of the patient's body is imaged by the capsule endoscope and pieces of the image data obtained thereby are transmitted from the capsule endoscope by way of wireless communications. The receiver 201 receives those pieces of image data and stores them in the patient information storage unit 205 under the control of the control circuit 207. Likewise, the receiver 202 also receives pieces of image data and stores them in the patient information storage unit 206 under the control of the control circuit 208.

After each capsule endoscope is ejected to outside of each patient's body, the receivers 201 and 202 are detached from the patients and the process proceeds to S105, in which the operator mounts the two receivers onto the two cradles. In this event, the combination between the receivers and cradles are discretionary and therefore the operator needs not to be concerned about the combination.

The following description is provided by exemplifying the case in which the two receivers are mounted onto the cradles in the order reverse to the event of the initialization. That is, the operator inserts the receiver 201 into the slot of the cradle 102, and inserts the receiver 202 into the slot of the cradle 101, in S105 shown in FIG. 4.

Then, two records are created in the slot correspondence table 401 on the RAM 303 of the observation apparatus 301 in S106. As a result, the slot correspondence table 401 becomes as shown in FIG. 3. Note that the patient information 421 according to the present embodiment is the information that includes "01" as the patient ID, "male" as the sex and "1950/05/05" as the birth date, as shown in FIG. 5. Meanwhile, the patient information 422 according to the present embodiment is the information that includes "02" as the patient ID, "female" as the sex and "1953/04/04" as the birth date.

That is, when the receiver 202 is inserted into the slot of the cradle 101 in S105, the communication I/F 311 connected to the cradle 101 detects the insertion and reports the event to the CPU 304 in S106. Triggered by the report, the CPU 304 instructs the receiver 202 mounted onto the cradle 101 to transmit the patient information stored in the patient information storage unit 206. Then, the receiver 202 transmits the patient information 422 to the observation apparatus 301 in accordance with the instruction. The CPU 304 associates the patient information 422 received at the communication I/F 311 with the port address 411 of the communication I/F 311, and generates a new record in the slot correspondence table 401.

Likewise, when the receiver 201 is inserted into the slot of the cradle 102 in S105, a record associating the port address 412 and patient information 421 with each other is generated in the slot correspondence table 401. As a result, the slot correspondence table 401 becomes as shown in FIG. 3.

Then, the CPU 304 performs a control for displaying the patient information on the LCD 306 of the observation apparatus 301 in S107. FIG. 6 is a diagram exemplifying the screen 504 of the LCD 306 in S107. In accordance with the contents of the slot correspondence table 401, the screen 504 displays the patient information 422 by correlating with the cradle ID being "cradle 101" and the patient information 421 by correlating with the cradle ID being "cradle 102".

Here, comparing the slot correspondence table 401 shown in FIG. 3 with FIG. 6, the port addresses 411 and 412 are used as the slot ID identifying a slot in the slot correspondence table 401, while the cradle IDs are used in the screen 504 of FIG. 6.

As described above, the first embodiment makes it possible to use a port address, or a cradle ID, for identifying a slot because the port address, cradle and slot uniquely correspond to one another (i.e., 1:1:1 relationship). The first embodiment is an example using two kinds of information for identifying a slot.

The operator can be enabled to visually identify the cradle 101 and 102 if, for example, labels, on which the respective cradle IDs are written, are pre-attached on the cradles 101 and 102, respectively. In the meantime, a port address is a value managed within the observation apparatus 301 and therefore it is not suitable to a usage such as the operator discerning a port at a glance. Accordingly, the first embodiment is configured to use suitably, that is, to utilize a port address in the slot correspondence table 401, and to display the identification number of a cradle in the screen 504. For implementing the suitable use a fixed relationship between a port address and a cradle ID is pre-stored in the hard disk 307. Then, the relationship is read out to, for example, the RAM 303 in S107. This configuration enables the operator to confirm that the receivers having been equipped on the patients with the patient IDs being "02" and "01", respectively, are mounted onto the cradles 101 and 102, only by looking at the screen 504.

Further, the screen 504 shown in FIG. 6 also displays a button labeled as "start transfer". Now the description returns to FIG. 4. When the operator uses, for example, a mouse to click on the button in order to instruct the observation apparatus 301 to start the transfer of image data, the process proceeds from S107 to S108. The image data stored in the two receivers are transferred (i.e., transmitted) to the observation apparatus 301 in S108.

The first embodiment assumes that the sequence of transfer is predetermined to be "the sequence of the cradle 101 first followed by the cradle 102". Therefore, the transfer of the image data to the observation apparatus 301 starts with that from the receiver 202 mounted onto the cradle 101 in S108. Then, after the completion of the transfer from the receiver 202, the transfer of the image data to the observation apparatus 301 from the receiver 201 mounted onto the cradle 102 is carried out. The transfer of the image data in S108 is controlled by the CPU 304 of the observation apparatus 301. That is, the control circuit 207 of the receiver 201 and the control circuit 208 of the receiver 202 transfer the image data to the observation apparatus 301 at respective timings instructed by the observation apparatus 301. During the transfer of the image data, a screen 505 as shown in FIG. 7 is displayed on the LCD 306 of the observation apparatus 301.

Comparing FIG. 7 with FIG. 6, the difference is where there is no "start transfer" button and there are instead progress bars indicating the progress of the transfer of image data being displayed corresponding to two cradle IDs, respectively, in the former. The screen 505 shown in FIG. 7 exemplifies the stage in which the transfer of the image data from the cradle 101 to the observation apparatus 301 is approximately one-third completed and the transfer of the image data from the cradle 102 to the observation apparatus 301 is not yet started.

As described above, the first embodiment is configured such that merely clicking on the "start transfer" button causes sequential transfers of image data from the two receivers to the observation apparatus 301. Therefore, the configuration enables the operator to be engaged in another work without an interruption until the transfer from both the receivers 202 and 201 is completed after clicking on the "start transfer" button. Further, such an operation is clearly the same if the number of receivers is three or more. Therefore the first embodiment of the present invention makes it possible to improve the work efficiency of the operator better than that can be achieved by the conventional system even if a receiver having a built-in patient information storage unit is used.

In the meantime, when a plurality of patients is examined one after another, there is sometimes a need to equip new patients with receivers one after another by reusing the receivers as soon as the transfer of image data is completed therefrom. Even in such a case, the operator is merely required to take a glance at the screen 505 of FIG. 7 to be able to recognize whether or not there is a progress bar that indicates a 100% progress state, that is, whether or not there is a receiver that is ready for a reuse with the transfer of image data completed. Further, the configuration also enables the operator to easily grasp as to which receiver has accumulated whose image data and what progress each receiver is in, in terms of the transfer of image data therefrom. Therefore, it is also easy to devise a plan for reusing the receivers in accordance with the progress.

Meanwhile, the CPU 304 of the observation apparatus 301 may control the LCD 306 also for parts other than the progress bars of the screen 505 so as to change display contents in accordance with the transfer state (i.e., transfer progress) of image data, such as "transfer in progress" and "transfer complete".

As an example, the CPU 304 may control the color, brightness, blinking pattern and/or the like, which are used to display information related to a receiver (i.e., the cradle ID and patient information), which is displayed on the screen 505. Alternatively, the CPU 304 may control the LCD 306 so as to display the information by changing the combination between the color, brightness, blinking pattern and the like in accordance with the transfer state of image data. It is possible to clearly show a receiver currently transferring image data on the screen 505 by means of such a control in accordance with the transfer state of image data.

Further, such a configuration also enables the operator to discern as to which cradle a receiver ready to be reused is mounted on, only by looking at the screen 505 if there is the receiver ready to be reused. The reason is that each progress bar is displayed corresponding to each cradle ID as shown in FIG. 7. This enables the operator to detach the receiver, which is ready to be reused, from the cradle and use it for examining a new patient. Note that the operator is preferably advised to compare the patient information displayed on the LCD of the receiver with the screen 505 of the LCD 306 of the observation apparatus 301 in order to prevent erroneously detaching, from the cradle, a receiver from which the transfer of image data has not yet completed.

As an example, as the data transfer from the receiver 202 mounted onto the cradle 101 further progresses and completes, the operator looks at the progress bar displayed corresponding to the cradle 101 and accordingly recognizes that it shows a 100% progress, in the example shown in FIG. 7. That is, the operator recognizes that the receiver can be detached from the cradle 101.

In this event, the operator visually compares the screen 505 on the LCD 306 of the observation apparatus 301 with the screen on the LCD 204 of the receiver 202 mounted on the cradle 101 and confirms that the same patient information is displayed. This operation prevents the receiver 201, which has not completed the transfer of image data, from being wrongly detached from the cradle 102. Further, if a label on which the cradle ID is written is pre-attached to each cradle as described above, it is possible to prevent a mistake further securely by the operator further visually comparing the cradle ID written on the label with the cradle ID displayed in the screen 505.

As described above, the first embodiment makes it possible to visually discern a receiver, which has completed transferring image data, by its appearance, thereby enabling a reuse of the receiver efficiently, while preventing a mistake, by carrying out a simple operation. Further, compared with the case of using a receiver configured to accumulate image data in a removable storage medium, the first embodiment of the present invention is configured to eliminate an operator operation to attach or detach a storage medium, thereby reducing the work load of the operator and excelling in operability.

Figure 8:
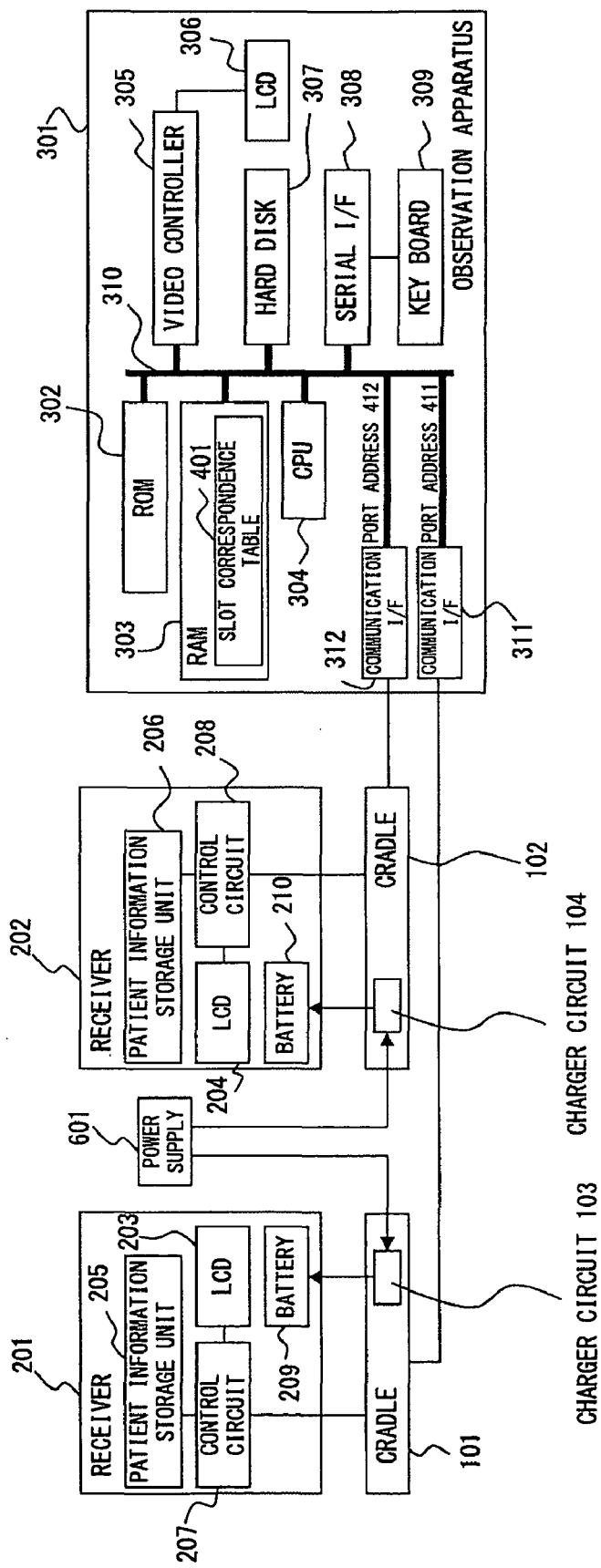
FIG. 8 is a block diagram showing the configuration of a capsule-type endoscope system according to a second embodiment of the present invention.
Figure 9:
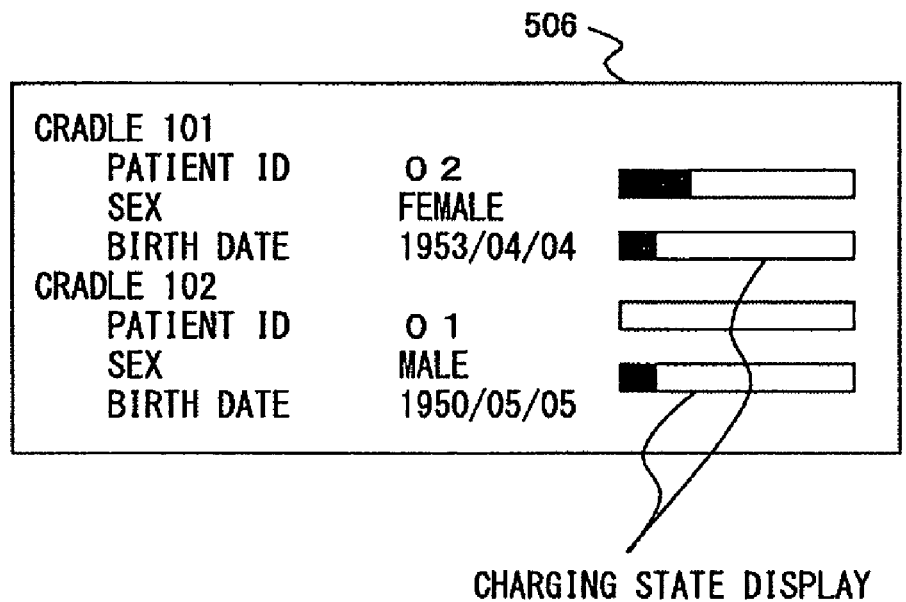
FIG. 9 is a diagram exemplifying the screen of an observation apparatus displayed when image data is transferred in a second embodiment of the present invention.

Next is a description of a second embodiment of the present invention by referring to FIGS. 8 and 9. Note that the same reference sign is assigned to the same constituent component as that of the first embodiment, and the description is abridged as appropriate.

FIG. 8 is a block diagram showing the configuration of a capsule type endoscope system according to the second embodiment of the present invention. The difference from the first embodiment shown in FIG. 2 lies in the following paragraphs (a) and (b).

(a) The cradles 101 and 102 respectively include charger circuits 103 and 104, which are connected to an external power supply 601; and (b) The receivers 201 and 202 respectively include batteries 209 and 210 that are charged respectively by way of the charger circuits 103 and 104.

That is, the battery 209 is a rechargeable battery that is electrically connected to the charger circuit 103 or 104 when the receiver 201 is mounted onto the cradle 101 or 102, and the battery 209 is charged from the power supply 601 by way of the charger circuit 103 or 104. This is similar for the battery 210.

FIG. 9 is a diagram exemplifying the screen 506 on the LCD 306 of the observation apparatus 301 displayed when image data is transferred from a receiver to the observation apparatus 301 in the second embodiment. The difference between the screen 505 shown in FIG. 7 displayed in the step S108 of the first embodiment and the screen 506 shown in FIG. 9 is where the progress of the charging is also displayed in the latter configuration while being associated with each cradle ID. The batteries 209 and 210 are simultaneously and parallelly charged in the two cradles as shown in FIG. 9.

As such, the second embodiment is configured to display the progress of charging and that of an image data transfer together in one screen 506. Therefore, this configuration enables the operator to easily identify, and reuse, a receiver that is ready to reuse after completing a data transfer and sufficient charging. Further, the time can be effectively used by charging the battery in parallel with the image data transfer.

Figure 10:
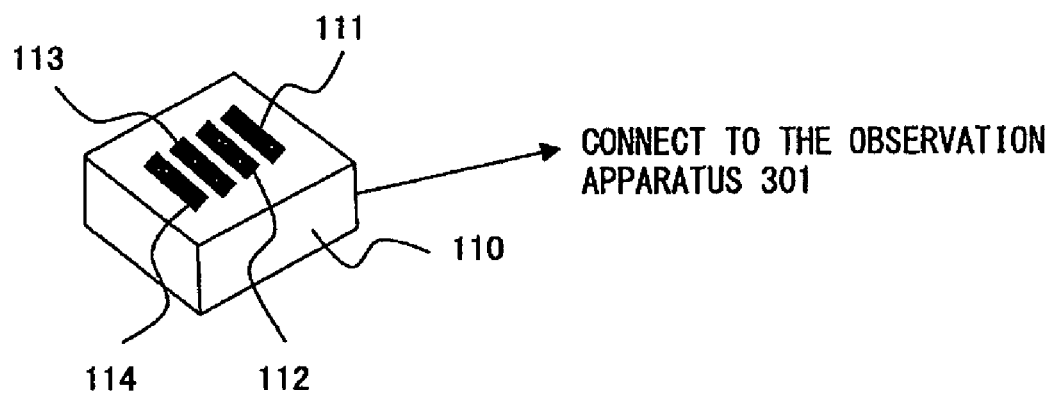
FIG. 10 is a perspective view of a cradle used in a third embodiment of the present invention.
Figure 11:
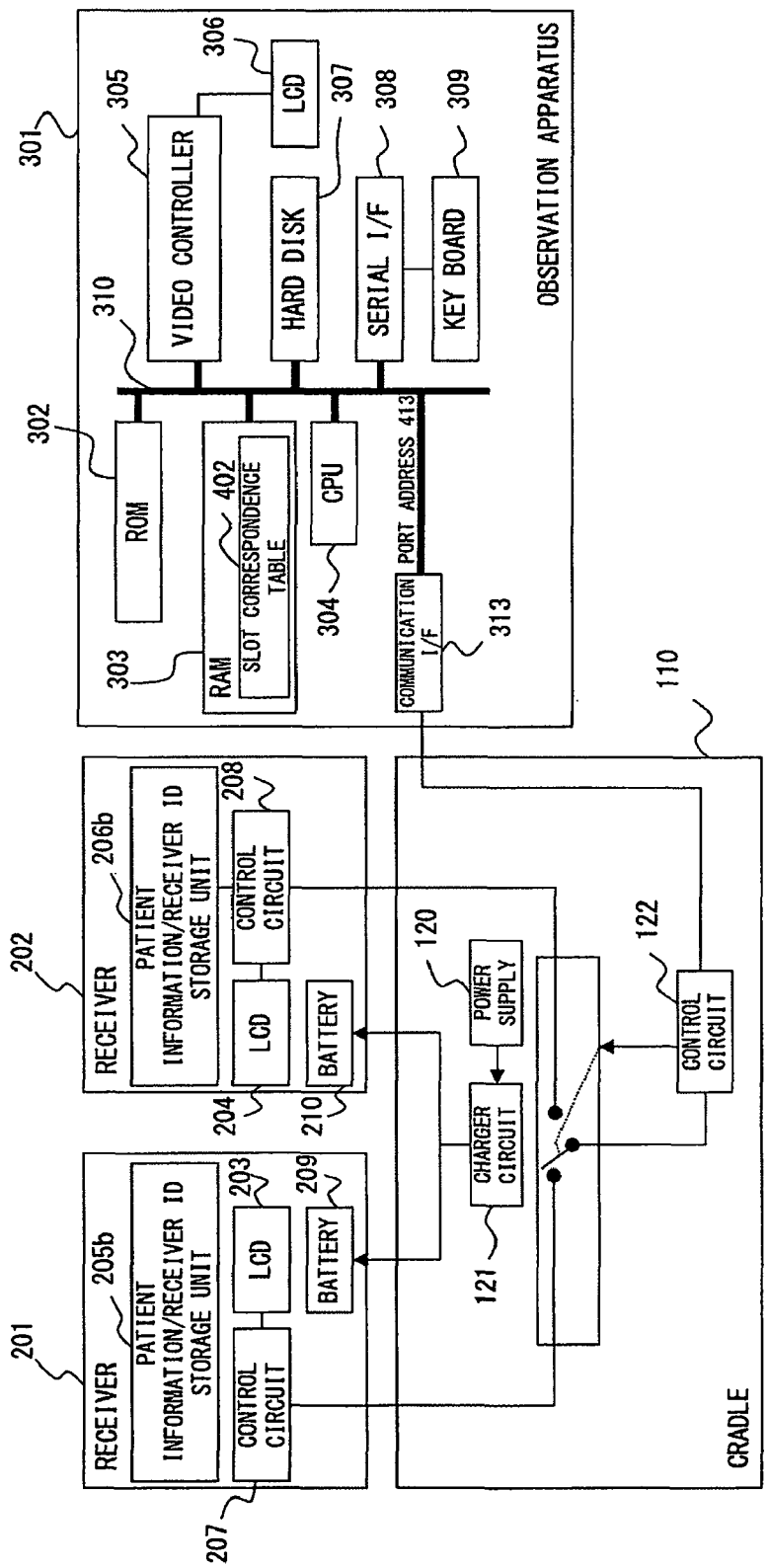
FIG. 11 is a block diagram showing the configuration of a capsule-type endoscope system according to a third embodiment of the present invention.

Next is a description of a third embodiment of the present invention by referring to FIGS. 10, 11 and 12. Note that the same reference sign is assigned to the same constituent component as those of the first and second embodiments, and the description is abridged as appropriate.

FIG. 10 is a perspective view of a cradle used in the third embodiment of the present invention. The third embodiment is configured such that a cradle has a plurality of slots for inserting receivers. As an example, the cradle 110 shown in FIG. 10 has four slots 111 through 114. In the third embodiment, a mounting spot is embodied by each of the slots 111 through 114 of the cradle, likewise the case of the first and second embodiments. A plurality of receivers can be collectively connected to an observation apparatus 301 by way of the cradle 110, which has a plurality of slots corresponding to the above described mounting spots as well as a cable connecting the cradle 110 to the observation apparatus 301.

If there are many receivers to be simultaneously connected to the observation apparatus 301 in order to transfer pieces of image data in a lump, the present embodiment has an advantage of the cradle 110 occupying a smaller space than the case of using a number of cradles such as the first embodiment.

FIG. 11 is a block diagram showing the configuration of a capsule-type endoscope system according to the third embodiment of the present invention. The difference from the second embodiment shown in FIG. 8 is due to the configuration where the cradle 110 has a plurality of slots. Note that FIG. 11 indicates only a part corresponding to two of the four slots 111 through 114 due to space limitations.

In the configuration of FIG. 11, only one cradle 110 is connected to the observation apparatus 301, and therefore it is sufficient for the observation apparatus 301 to have only one communication I/F 313. A port address 413 is assigned to the communication I/F 313.

The cradle 110 includes a control circuit 122 for selecting a slot and controlling the transmission of data between a receiver inserted into the selected slot and the observation apparatus 301. Likewise the step S108 of the first embodiment, the present third embodiment is also configured such that the control circuit 122 changes over the selections of slots at the timing in accordance with an instruction from the CPU 304 of the observation apparatus 301. The changeover is carried out automatically and thereby the degree of operator intervention is reduced from the conventional system.

Likewise the cradles 101 and 102 of FIG. 8, the cradle 110 also includes a charger circuit 121. The charger circuit 121 is configured to charge a plurality of receivers inserted into a plurality of slots simultaneously and parallelly. The power supply 120 supplies the charger circuit 121 with the power.

Receivers 201 and 202 shown in FIG. 11 are configured approximately equivalent to the receivers 201 and 202 shown in FIG. 8, with an exception that patient information/receiver ID storage units 205b and 206b are equipped in place of the patient information storage units 205 and 206 shown in FIG. 8. Each of the patient information/receiver ID storage units 205b and 206b also stores a receiver ID identifying a receiver, in addition to the patient information and image data, both of which are equivalent to those stored by the patient information storage units 205 and 206. A receiver ID may be a production serial number which is assigned, for example, when a receiver is produced and which is stored in the patient information/receiver ID storage unit 205b or 206b.

The following description is provided by assuming that the receiver IDs of the receivers 201 and 202 are respectively "3457" and "3458". That is, the patient information/receiver ID storage units 205b and 206b respectively pre-store "3457" and "3458" as the respective receiver IDs.

Further assumption is that, likewise the first embodiment, the receivers 201 and 202 are respectively initialized with the patient information related to the patients identified by the patient IDs being "01" and "02", respectively, and are used for examining the respective patients. That is, the patient information containing the patient ID of "01" is written to the patient information/receiver ID storage unit 205b of the receiver 201 as a result of the initialization. The patient information containing the patient ID of "02" is likewise written to the patient information/receiver ID storage unit 206b of the receiver 202 as a result of the initialization.

FIG. 12 is a diagram exemplifying a slot correspondence table according to the third embodiment of the present invention. Compared with the slot correspondence table 401 of the first embodiment shown in FIG. 3, the difference is where a receiver ID is used in place of the port address in the present embodiment. FIG. 12 specifically shows an example of the patient information being constituted by patient ID, sex and birth date.

Likewise the process of the first embodiment described by referring to the steps S105 and S106 shown in FIG. 4, a record is created in the slot correspondence table 402 of FIG. 12 when a receiver, after completing an examination, is inserted into any one of the slots of the cradle 110.

When, for example, the receiver 201 is inserted into the slot 112, the insertion is detected by the communication I/F 313 by way of the cradle 110 and is reported to the CPU 304. Triggered by the report, the CPU 304 then instructs the receiver 201 to transmit the receiver ID and patient information, which are stored in the patient information/receiver ID storage unit 205b. As a result, the receiver ID, i.e., "3457" and the patient information are read from the patient information/receiver ID storage unit 205b and transmitted to the observation apparatus 301, where the patient information is constituted by the patient ID, i.e., "01", the sex, i.e., "male", and the birth date, i.e., "1950/05/05". Then, the first record is created in the slot correspondence table 402. The second record is also created in a similar manner.

The receiver ID may be, for example, the production serial number of a receiver, or any other number. The third embodiment is configured to preattach a label, on which a receiver ID is written, to each receiver. When image data is transmitted from a receiver to the observation apparatus 301, the CPU 304 controls, by way of the video controller 305, the LCD 306 so as to display a screen containing the receiver IDs in place of the cradle IDs in the screen 506 shown in FIG. 9. This enables the operator to simply recognize the progress of an image data transmission from each receiver and the progress of charging by visually comparing the labels and LCDs 203 and 204 of the receivers 201 and 202 with the LCD 306 of the observation apparatus 301. Further, both the receiver ID and patient information are visually recognizable, and therefore the configuration enables the operator to select a receiver, which has completed an image data transmission and charging, more securely than the case of using only either one of the receiver ID or patient information.

Note that the present invention may be embodied with various modifications, in lieu of being limited to the embodiments described above. The following provides a few examples.

It is clearly possible for the operator to mount the receiver 201 onto the cradle 101 and the receiver 202 onto the cradle 102 in step S105 shown in FIG. 4. Also in this case, records are created in the slot correspondence table in a similar manner to the above description.

The sequence of an image data transfer from a plurality of receivers to the observation apparatus 301 is discretionary, depending on the embodiments. The first embodiment described above is configured to predetermine the sequence. It is also possible that pieces of the image data is transferred in the sequence designated via the key board 309 or the like operated by an operator. Alternatively, when pieces of image data are transferred from, for example, two receivers 201 and 202, the CPU 304 may control and alternately change over the transfer from the receiver 201 and that from the receiver 202 so that a constant amount of image data is transferred alternately from the receivers 201 and 202 to the observation apparatus 301.

The observation apparatus 301 may include a plurality of CPUs. The respective CPUs may be configured to be able to control a plurality of respective communication interfaces (I/Fs) independently. In such a case, the plurality of CPUs may respectively control the transfer independently so as to carry out the transfers from a plurality of receivers simultaneously and parallelly via a plurality of respective cradles connected to the plurality of respective communication I/Fs.

Further, while a plurality of cradles is separately connected to the observation apparatus 301 in the configurations of FIGS. 2 and 8, it is alternatively possible to adopt a configuration of connecting one hub device to the observation apparatus 301 and connecting a plurality of cradles to the hub device, respectively. Further possibility lies in intermixing a cradle having only one slot with a cradle having a plurality of slots. A cradle may be connected to the observation apparatus 301 by way of a wireless communication, in place of a cable.

Further, there are various types of cradles depending on the embodiments described above. The difference in types lies in whether or not a cradle includes a charger circuit, or how many slots one cradle has, or the like. There may be, however, an embodiment using different types of cradles in mixture. In the case of different types of cradles intermixed, the above described plurality of mounting spots is implemented by a plurality of slots distributed to a plurality of cradles.

As is clear from the comparison between the slot correspondence table 401 shown in FIG. 3 and the slot correspondence table 402 shown in FIG. 12, the present invention can be implemented only if the observation apparatus 301 is capable of managing the correlation (i.e., correspondence) between a receiver and a patient ID. That is, only if information identifying a patient is correlated (i.e., associated) with information identifying a receiver indirectly or directly, the correlation may be managed in a form other than a table form such as the slot correspondence table.

An example of information directly identifying a receiver is the receiver ID noted in the third embodiment. The following paragraphs (a) through (c) list the examples of information indirectly identifying a receiver.

(a) The ID of the slot in which a receiver is inserted, in the case of using a cradle having a plurality of slots.

(b) The ID of a cradle, in the case of there being one-to-one relationship between a slot and a cradle.

(c) The port address of a communication I/F, in the case of there being one-to-one-to-one relationship between a slot, a cradle and a communication I/F of the observation apparatus 301.

Further, in the case of, for example, there being one-to-one relationship between a slot and a cradle, the production serial number of a cradle may be used as the information indirectly identifying a receiver. In this case, if a label, on which the production serial number is written, is attached to the surface of a cradle, the operator can visually recognize the production serial number of the cradle easily.

Further, as described above, the first embodiment is configured to use a port address in the slot correspondence table 401, and, on the other hand, display a cradle ID on the LCD 306 of the observation apparatus 301. For this configuration, a fixed correlation between the port address and cradle ID is managed. It is clear that such a management will be somewhat unnecessary depending on the contents to be displayed on the LCD 306, and that the information to be managed also differs, depending on the embodiments.

A receiver may further be equipped with an illumination device, such as a lamp, as a countermeasure to preventing a wrong detachment of a receiver that has not completed an image data transfer when an operator attempts to detach a receiver for a reuse. Such a device indicates whether or not a data transfer has been completed by means of the lighting, blinking or color of a lamp, or a combination of the aforementioned controls of the lamp so as to facilitate the operator to confirm the lamp in addition to the LCD, thereby preventing a mistake further securely.

Further, a cradle may be equipped with a locking mechanism for mechanically locking a receiver in a slot of the cradle in order to prevent the receiver that has not completed an image data transfer from being wrongly detached from the cradle. That is, such a locking mechanism is configured to be engaged when an image data transfer is started so as to retain the receiver by fixing it in the slot to prevent the receiver from detaching from the slot of the cradle and to be disengaged when the image data transfer is completed.

Alternatively, the CPU 304 of the observation apparatus 301 may instruct the control circuit of a receiver, which has completed an image data transfer, to delete the entirety of data. For example, when an image data transfer from the receiver 201 is completed, the control circuit 207 of the receiver 201 deletes the entirety of the data stored in the patient information storage unit 205 in accordance with the instruction from the CPU 304 of the observation apparatus 301.

As a result, there is no longer the data to be displayed on the display unit 203, which implements the first display unit, in the receiver 201. The control circuit 207 may control the display unit 203 so as to display nothing after deleting the data. This configuration enables the operator to easily recognize that a receiver that may be detached from the cradle is only the receiver displaying nothing on the display unit. Therefore, such a data deletion and a display control also make it possible to prevent a receiver, which has not completed an image data transfer, from being wrongly detached from the cradle.

Further, the screen 505 of FIG. 7 and the screen 506 of FIG. 9 exemplify a progress bar as the display of a progress; it is alternatively possible to indicate the progress by means of characters such as "will complete in n minutes" (where "n" is a number) Further, the CPU 304 of the observation apparatus 301 may control the LCD 306 so as to display the speed of transferring image data, for example, in units of bits per second (bps) and thereby displaying the progress of the image data transfer in the screen 505 or 506. Furthermore, the progress of an image data transfer and/or that of charging may be displayed on a receiver.

Note that pieces of the patient information, which are displayed on the respective LCDs of the receiver and observation apparatus 301, are not limited to the exemplified combination. Depending on the embodiments, another piece of information, such as a patient's name, may be displayed or a part of the exemplified pieces of patient information may be eliminated from the contents to be displayed.

As described above, the embodiments of the present invention make it possible to transfer image data in a lump by collectively connecting a plurality of receivers, each of which is equipped with a built-in patient information storage unit functioning as the first storage unit, to an observation apparatus. It is therefore possible to reduce the actual working hours of an operator or the number of times an operator is required to interrupt another work.

Further, the embodiments of the present invention enable the operator to recognize the progress of a transmission from each receiver by visually comparing the respective LCDs of the receiver and observation apparatus, which function as the first and second display units, respectively. That is, the configuration enables the operator to easily discern a receiver that is ready for a reuse at the completion of an image data transfer. Therefore, the embodiments described above enables a reuse of the receiver efficiently without requiring a complex operation or degrading operability.

Further, an embodiment in which the charging condition of each receiver is displayed in the screen 506 on the LCD 306, which functions as the second display unit, of the observation apparatus 301 enables the operator to easily determine whether or not a receiver is ready for a reuse while considering the charging condition of the receiver.

What is claimed is:

1. A capsule-type endoscope system, comprising:
a plurality of receivers each for receiving, from a capsule-type endoscope by way of a wireless communication, image data of an observation image of inside of a body of an examinee imaged by the capsule-type endoscope;
a plurality of mounting spots for respectively mounting the plurality of receivers; and
an information processing apparatus connected to the plurality of receivers by way of the respective mounting spots, wherein each of the plurality of receivers comprises a first storage unit and a first display unit,
the first storage unit stores the received image data and examinee identification information identifying the examinee,
the first display unit displays the examinee identification information or examinee information about the examinee that is associated with the examinee identification information,
the information processing apparatus comprises:
a management unit for receiving the examinee identification information from each of the plurality of receivers by way of each of the plurality of mounting spots and managing correlation between the received examinee identification information and receiver identification information identifying the receiver or mounting spot identification information identifying the mounting spot on which the receiver is mounted,
a second storage unit, and
a second display unit,
the image data is transmitted to the information processing apparatus by way of each of the plurality of mounting spots and stored in the second storage unit,
the second display unit displays the correlation by displaying at least a part of the examinee identification information displayed on the first display unit or a part of the examinee information displayed on the first display unit, and
the second display unit further displays a progress of the transmission of the image data corresponding to each of the plurality of receivers.

2. The capsule-type endoscope system according to claim 1, wherein
the plurality of mounting spots is a plurality of slots provided in at least one cradle device.

3. The capsule-type endoscope system according to claim 1, wherein
the plurality of mounting spots is a plurality of slots provided in a plurality of respective cradle devices.

4. The capsule-type endoscope system according to claim 3, wherein
the mounting spot identification information is either
port identification information identifying a plurality of ports comprised in the information processing apparatus to enable the plurality of cradle devices to be connected, respectively, or
cradle device identification information identifying the plurality of cradle devices.

5. A non-transitory computer readable storage medium storing a program to direct an information processing apparatus to execute a process, wherein
the information processing apparatus is connected to a plurality of receivers by way of a plurality of mounting spots, respectively, in a capsule-type endoscope system,
the capsule-type endoscope system comprises:
the plurality of receivers each for receiving, from a capsule-type endoscope by way of a wireless communication, and storing, image data of an observation image of inside of a body of an examinee imaged by the capsule-type endoscope, and for storing examinee identification information identifying the examinee, and
the plurality of mounting spots enabling the plurality of receivers to be mounted, respectively, and
the process comprises the steps of:
detecting that any of the receivers is mounted on any of the mounting spots, receiving the examinee identification information from the detected receiver by way of the mounting spot, associating receiver identification information identifying the detected receiver, or mounting spot identification information identifying the detected mounting spot, with the received examinee identification information, storing correlation as a result of the associating, displaying the correlation by displaying at least a part of the examinee identification information displayed in each of the plurality of receivers or a part of examinee information about the examinee displayed in each of the plurality of receivers, wherein the examinee information is associated with the examinee identification information, receiving the image data transmitted from the detected receiver by way of the mounting spot, and displaying at least either a progress of the transmission or a speed of the transmission.

6. The capsule-type endoscope system according to claim 3, wherein
at least one of the plurality of cradle devices comprises a charger circuit for charging the receiver in parallel with the receiver mounted on the slot transmitting the image data.

7. The capsule-type endoscope system according to claim 1, wherein
at least either the first display unit of the receiver or the second display unit of the information processing apparatus displays a charging state of the receiver.

8. The capsule-type endoscope system according to claim 1, wherein
the receiver comprises an illumination device for indicating a transfer state of the image data.

9. The capsule-type endoscope system according to claim 1, wherein
at least either the first display unit of the receiver or the second display unit of the information processing apparatus displays at least either a figure or a character indicating a transfer state of the image data.

10. The storage medium according to claim 5, wherein the process further comprises at least either
a step of indicating a charging state of the receiver or
a step of controlling the receiver so as to indicate the charging state of the receiver.

11. The storage medium according to claim 5, wherein the process further comprises at least either
a step of indicating a transfer state of the image data by means of at least either a figure or a character or
a step of controlling the receiver so as to indicate the transfer state of the image data by means of at least either a figure or a character.

12. The capsule-type endoscope system according to claim 1, further comprising
a control unit for controlling the second display unit so as to display information corresponding to the receiver while changing at least any one of color, brightness and blinking pattern in accordance with the progress of the transmission of the image data when the image data stored in the first storage unit of each of the plurality of receivers is transmitted to the information processing apparatus.

13. The capsule-type endoscope system according to claim 1, further comprising
a control unit for selecting a sequence of transferring individual pieces of the image data stored in the respective first storage units of the plurality of receivers to the information processing apparatus.

14. The capsule-type endoscope system according to claim 1, further comprising
a control unit for selecting any one of a plurality of choices related to a transfer method to be used when individual pieces of the image data stored in the respective first storage units of the plurality of receivers are transferred to the information processing apparatus, wherein
the plurality of choices include at least one of
a serial transfer that carries out, sequentially for each of the plurality of receivers, a process for transferring entirety of the image data from the first storage unit of one of the receivers currently concerned to the information processing apparatus,
an alternate transfer that repeats transferring respective parts of the image data stored in the respective first storage units of the plurality of receivers alternately from the plurality of receivers to the information processing apparatus, and
a parallel transfer that transfers, simultaneously and parallelly, individual pieces of the image data from the respective first storage units of the plurality of receivers to the information processing apparatus.

15. The capsule-type endoscope system according to claim 1, further comprising
a retention unit for mechanically fixing the receiver transferring the image data in order to prevent the receiver from being detached from the mounting spot.

16. The capsule-type endoscope system according to claim 1, wherein
at least either the first display unit of the receiver or the second display unit of the information processing apparatus indicates at least either a transfer state of the image data or a transfer speed of the image data by means of at least either a figure or a character.

17. The storage medium according to claim 5, wherein the process further comprises a step of displaying information corresponding to the receiver while changing at least any one of color, brightness and blinking pattern in accordance with the progress of the transmission of the image data when the image data stored in the plurality of receivers is transmitted to the information processing apparatus.

18. The storage medium according to claim 5, wherein the process further comprises a step of selecting a sequence of transferring the image data stored in the plurality of receivers to the information processing apparatus.

19. The storage medium according to claim 5, wherein the process further comprises at least either
a step of indicating at least either a transfer state of the image data or a transfer speed of the image data by means of at least either a figure or a character, or
a step of controlling the receiver so as to indicate at least either the transfer state of the image data or the transfer speed of the image data by means of at least either a figure or a character.

20. A method executed by an information processing apparatus in a capsule-type endoscope system comprising a plurality of receivers, a plurality of mounting spots enabling the plurality of receivers to be respectively mounted, and the information processing apparatus connected to the plurality of receivers respectively by way of the mounting spots, comprising:
detecting that any of the receivers is mounted on any of the mounting spots;

receiving, from the detected receiver by way of the mounting spot, examinee identification information identifying an examinee whose body has been imaged from inside by a capsule-type endoscope as an observation target of image data of an observation image of the inside of the body, while the image data being stored by the detected receiver as a result of having received from the capsule-type endoscope by way of a wireless communication;

associating the received examinee identification information with receiver identification information identifying the detected receiver, or mounting spot identification information identifying the detected mounting spot, storing correlation as a result of the associating;

displaying the correlation by displaying at least a part of the examinee identification information displayed in each of the plurality of receivers or a part of examinee information about the examinee displayed in each of the plurality of receivers, wherein the examinee information is associated with the examinee identification information;

receiving the image data transmitted from the detected receiver by way of the mounting spot; and displaying at least either a progress of the transmission or a speed of the transmission.

* * * * *